United States Patent [19]

Fry

[11] 3,948,716

[45] Apr. 6, 1976

[54] PREPARATION OF MOULDING COMPOUNDS

[75] Inventor: David Philip Fry, Cardiff, Wales

[73] Assignee: BP Chemicals International Limited, Great Britain

[22] Filed: Oct. 1, 1973

[21] Appl. No.: 401,977

[30] Foreign Application Priority Data
Oct. 11, 1972  United Kingdom............... 46786/72

[52] U.S. Cl. ................ 156/324; 156/549; 427/180; 427/390; 428/228; 428/246
[51] Int. Cl.² ........................................... C09J 5/06
[58] Field of Search ........... 156/237, 241, 289, 314, 156/315, 316, 324, 537, 547, 549, 550; 161/232; 117/62.2, 126 GB; 260/865; 427/180, 390; 428/228, 246

[56] References Cited
UNITED STATES PATENTS

| | | | |
|---|---|---|---|
| 3,536,642 | 10/1970 | Williger et al. | 260/22 |
| 3,734,814 | 5/1973 | Davis, Sr. et al. | 161/112 |

FOREIGN PATENTS OR APPLICATIONS

| | | | |
|---|---|---|---|
| 576,533 | 5/1959 | Canada | 156/315 |

Primary Examiner—William A. Powell
Assistant Examiner—Brian J. Leitten

[57] ABSTRACT

A process for the preparation of unsaturated polyester resin based sheet moulding compounds in which the compound is matured by including a gelling agent for the copolymerisable monomer in the resin matrix and subjecting the sheet moulding compound to a temperature sufficient to cause the gelling agent to gel the copolymerisable monomer without activating the polymerisation initiator.

14 Claims, No Drawings

PREPARATION OF MOULDING COMPOUNDS

The present invention relates to a process for the preparation of fibre reinforced unsaturated polyester resin based thermosetting moulding compounds.

Thermosetting unsaturated polyester resin based moulding compounds are well known and consist essentially of an unsaturated polyester resin, an ethylenically unsaturated copolymerisable monomer, inert mineral fillers, fibrous reinforcing fillers and a catalyst which initiates the cross-linking reaction between the copolymerisable monomer and the unsaturated polyester resin at the chosen moulding temperature. They are commonly used in two physical forms, i.e. dough moulding compounds and sheet moulding compounds. In dough (DMC), sometimes known as bulk (BMC) moulding compounds, the fibrous reinforcing filler is in the form of randomly dispersed short fibres, suitably of length about ¼ inch. In sheet moulding compounds (SMC) sometimes known as "prepreg" (preimpregnated mat), the fibrous reinforcing filler is present either as a continuous mat or as chopped fibres deposited on a supporting carrier which are impregnated with the unsaturated polyester resin system, giving rise to sheets of moulding compound in which the fibres have not been subjected to the degrading action of conventional moulding compound mixers.

To prepare SMC, a polyester resin system of relatively low viscosity is required, in order to thoroughly wet out the fibrous reinforcement. However, such a resin system has the disadvantage that it gives a product which is sticky, making cutting and handling difficult. To overcome this problem, additives are included in the polyester resin system to bring about a viscosity increase after impregnation. Typical additives used hitherto include the oxides and hydroxides of magnesium and calcium. These however, have the disadvantage that the viscosity build up is slow i.e. of the order of 24 hours or more, and tends to continue throughout the life of the SMC prior to moulding, until a point where the SMC is too stiff to be of practical use. these known additives are believed to bring about a linking of the carboxyl groups in the unsaturated polyester and the metal ions in the additives.

It is an object of the present invention to provide a process for the preparation of SMC in which the viscosity build up of the polyester resin system is achieved virtually instantaneously and does not continue up to a level where the SMC is unusable.

According to the present invention, a process for the preparation of an unsaturated polyester resin based sheet moulding compound comprises (i) impregnating a continuous web of fibrous reinforcement with a liquid unsaturated polyester resin system consisting essentially of an unsaturated polyester, a liquid copolymerisable monomer, a polymerisation initiator and a gelling agent for the copolymerisable monomer, said gelling agent being capable of forming stable gels of the copolymerisable monomer when heated to a temperature below the temperature at which cross-linking of the system occurs, and (ii) subsequently heating the impregnated web to a temperature sufficient to cause the gelling agent to gel the copolymerisable monomer.

Unsaturated polyesters for use in sheet moulding compositions are well known. See for example, British Patent Specification 1098132. The preferred unsaturated polyesters for use in the process of the present invention are those which have a relatively high hot rigidity in the thermoset state, so that any reduction of rigidity due to the presence of modifying agents is offset. Examples of such unsaturated polyesters are those in which more than 50 molar percent of their acidic residues are derived from maleic or fumaric acids. Examples are polypropylene glycol maleate or fumarate, or such unsaturated polyesters with a minor proportion of the maleic or fumaric residues replaced by iosphthalic or carbic acid residues. Also suitable are unsaturated polyesters containing more than 50 molar percent of maleic and fumaric acid residues and alcohol residues derived from Bisphenol A adducts with ethylene oxide or propylene oxide. Further suitable unsaturated polyesters are those in which a minor proportion of the maleic or fumaric acid residues are replaced by chloro-acid residues such as tetra-chlorophthalic or chlorendic acid residues.

The copolymerisable monomer is suitable a liquid monomer having ethylenic unsaturation for example styrene, vinyl toluene and diallyl phthalate. The amount of copolymerisable monomer used is suitably in the range from 20 to 60% by weight and preferably from 40 to 50% by weight based on the total weight of the unsaturated polyester resin and copolymerisable monomer.

The unsaturated polyesters hereinbefore described are generally very viscous liquids or solids at ambient temperatures and they are therefore dissolved in the liquid copolymerisable monomer to enable them to be used to satisfactorily impregnate the fibrous reinforcement.

Suitable polymerisation initiators for use in the process of the present invention are those known for use in thermosetting unsaturated polyester resin based moulding compounds. It is an essential feature of the present invention that the initiator used has a decomposition temperature that is higher than the temperature to which the unsaturated polyester/copolymerisable monomer mixture is heated to achieve gelation i.e. the chosen initiator does not initiate and sustain the vinyl polymerisation process at a significant level as this would result in the crosslinking of the unsaturated polyester and copolymerisable monomer at the temperature used for achieving gelation. They preferably have a decomposition temperature above 75°C and include benzoyl peroxide, methyl ethyl ketone peroxide, t-butyl hydroperoxide, t-butyl perbenzoate and di-t-butyl peroxide. The amount of peroxidic initiator used is suitably in the range 0.1 to 5.0% by weight based on the total weight of the unsaturated polyester/copolymerisable monomer mixture. Also suitable as initiators are 2,2$^1$-azobis-(2,4-dimethyl valeronitrile), 2,2$^1$azobis (2,4,4-tri-methyl valeronitrile), 2,2$^1$-azobis-(2,4-dimethyl-4-methoxy valeronitrile), 1,1$^1$-azobis-(cyclooctane carbonitrile), 2,2$^1$azobis (isobutyronitrile) and azo-1-cyanocyclohexane. The quantity of azo compound used is suitably in the range of 0.05 to 2.0% by weight, based on the total weight of the unsaturated polyester and the copolymerisable monomer.

By gelling agent is meant throughout this specification a substance which when heated to an elevated temperature in the chosen copolymerisable monomer causes the formation of a stable gel structure in the copolymerisable monomer. Preferably the gelling agent should also be capable of forming a stable gel when unsaturated polyester is dissolved in the copolymerisable monomer. However, certain unsaturated polyesters, especially those with little or no aromatic content, e.g. glycolmaleates, inhibit the gel formation process to the extent that a homogeneous stable gel is not formed, but there is still a sufficient viscosity increase on heating to the gel temperature to enable a satisfactory SMC to be prepared.

Suitable gelling agents include the aluminium salts of soap-forming carboxylic acids such as octoic, lauric, oleic, palmitic and stearic acids. Because aluminium is a trivalent metal it is possible to have up to three acid ions in each salt molecule. Where only one or two acid ions are present, it is preferred that the other ions are hydroxyl ions.

The amount of gelling agent necessary to form a stable gel of the copolymerisable monomer varies considerably depending on the choice of monomer and gelling agent and is readily determined by simple experimental work. In the case of styrene and aluminium palmitate it has been found that around 10% by weight of gelling agent, based on the weight of styrene, is a suitable amount. In general, amounts of from 5.0 to 20.0% by weight based on the amount of copolymerisable monomer are suitable.

The different gelling agents cause gelation to occur at different temperatures depending on the copolymerisable monomer and gelling agent selected. For example, when styrene is the monomer, aluminium octoate will cause gelation at 25°–35°C and the gelation temperature increases with aluminium octoate <aluminium oleate< aluminium palmitate <aluminium stearate. It will therefore be appreciated, that when using combinations of gelation agents and monomers in which the gelation temperatures are in the upper ranges, care must be taken to select a catalyst which will give an adequate margin between gelation temperature and the temperature at which cross-linking occurs to avoid inadvertant catalyst activation during gelation. When gelation agents and monomers are used in which the gelation temperature is in the lower ranges, care must be taken to ensure that the gelation temperature is not reached during the mixing of the resin system prior to its use for impregnating the fibrous reinforcement. It may, in fact, be necessary to cool the mixer to prevent premature gelation.

Suitably the liquid unsaturated polyester resin system constitutes from 20 to 40 wt % and preferably from 25–35 wt % of the total weight of the SMC prepared by the process of the present invention.

The fibrous reinforcement is suitably present in the form of a continuous sheet or as random fibres. Such fibrous reinforcing materials are well known in the art. The preferred fibrous reinforcing material is glass fibre, either in sheet form based on chopped strands or continuous filaments, or in the form of loose chopped strands. Suitably the sheet moulding compounds of the present invention contain from 5 to 40% by weight of fibrous reinforcement and preferably from 20 to 35% by weight of glass fibrous reinforcement based on the total weight of the SMC.

The unsaturated polyester resin system for use in the process of the present invention may further contain a mineral filler. Suitable mineral fillers for use in the SMC are those well known in the art for use in unsaturated polyester moulding compositions. The filler may consist entirely of a bulking filler, for example calcium carbonate, alumina, calcium sulphate, blanc fixe and clays, or may include additionally pigments, for example titanium dioxide, and fire retarding agents for example chlorinated paraffins, pentabromotoluene, and antimony oxide. The total weight of such fillers used in the sheet moulding compounds of the present invention is suitably in the range 20 to 60% by weight and preferably in the range 30 to 40% by weight, based on the total weight of the SMC.

In a preferred aspect of the present invention, a part of the inorganic filler is replaced by a modifier system to control the mould shrinkage. Such modifiers are known for use in thermosetting unsaturated polyester resin moulding compositions. By way of example, thermoplastic polymers, i.e. polystyrene, polyethylene, polyvinyl chloride and polyacrylate and polymethacrylates etc., when added to the compositions in an amount up to about 15% by weight of the total composition greatly reduce the mould shrinkage and such compositions are known as "low shrink" compositions. In a particularly preferred aspect of the present invention the modifier system comprises a combination of a saturated liquid polyester to prevent shrinkage and a thermoplastic polymer to prevent exudation of the saturated liquid polyester on moulding. Such a system enables mouldings having zero mould shrinkage or even an expansion when compared with the dimensions of the cold mould to be obtained and such compositions are known as "non-shrink" compositions. They are described in our British Patent specifications 1,098,132 and 1,250,631. Suitable saturated liquid polyesters for use in such systems include polypropylene adipate and polypropylene sebacate used at concentrations in the range 1 to 20% by weight and preferably 3 to 10% by weight on the total composition and suitable thermoplastics include polyvinyl chloride, polyethylene, polyacrylates, polymethacrylates and polystyrene used in an amount sufficient to prevent exudation of the saturated liquid polyester, suitable quantities being in the range 5 to 45% by weight and preferably 10 to 20% by weight of the quantity of saturated liquid polyester, although larger quantities can be used without deleterious effect. Particularly good results, in terms of the surface finish of the final moulded product, are obtained when the saturated liquid polyester is used in conjunction with a cellulose ester, eg cellulose acetate butyrate.

The polyester resin systems for use in the process of the present invention suitably further contain a vinyl polymerisation, inhibitor to prevent the premature polymerisation of the system on storage. Lubricants and mould release agents are generally present in the compositions in minor quantities.

In the process of the present invention the SMC may be prepared by passing a glass fibre mat through a polyester resin mix i.e. a mixture of the remaining ingredients of the sheet moulding compound as herein described, interleaving the wetted mat between polyethylene films and passing it through compression rolls to effect impregnation of the glass by the resin mix. Further kneading and compression may be carried out by ribbed rollers if required.

Alternatively sheet moulding compound may be prepared by coating layers of polyester resin mix onto polyethylene films, applying glass fibres produced by chopping glass rovings before bringing the films together to form a composite and passing this composite through compression rollers to effect impregnation of the glass by the resin mix.

Any other method suitable for the impregnation of fibrous reinforcement with a liquid unsaturated polyester resin system may be used in the process of the present invention.

After the SMC has been formed it is heated to a temperature sufficient to cause thickening and preferably gelation of the resin matrix but not high enough to cause activation of the catalyst. This is suitably effected by passing the SMC through banks of heaters, over heated rolls or by any other suitable means. Once the Matrix has reached the gelation temperature, the thickening or gel formation is almost instantaneous, and no further maturing of the compound is required before use.

The SMC prepared by the process of the present invention has the advantage that, because the resin monomer solution is gelled, exudation of resin components is minimised on storage. Further, because the gelation, unlike prior art maturation methods, does not rely on the formation of a chemical linkage between added metal ions and the carboxyl groups on the polyester, the acid number, hydroxyl content, free glycol content, and water content of the unsaturated polyester are not critical factors in the preparation of the SMC.

The invention will be further illustrated by the following example:

EXAMPLE:

A composition was prepared from the following components:- A 60% solution in styrene of an unsaturated polyester resin derived from 2 mol maleic anhydride, 1 mol isophthalic acid and 3.3 mol propylene glycol condensed to an acid

| | |
|---|---|
| value of 35 mg KoH per g | 30 p.b.w. |
| Hexaplas PPA (polypropylene adipate) | 8.0 p.b.w. |
| Cellulose acetate butyrate | 2.0 p.b.w. |
| t-butyl perbenzoate | 0.55 p.b.w. |
| Zinc stearate | 2.0 p.b.w. |
| Butylated hydroxy toluene | 0.05 p.b.w. |
| Styrene monomer | 2.0 p.b.w. |
| Dolomite (Microdol Extra) | 53.4 p.b.w. |
| Aluminium hydroxy di stearate | 2.0 p.b.w. |

77 p.b.w. of this composition were used to impregnate 25 p.b.w. of a chopped strand glass fibre mat on a polyethylene sheet and a further sheet of polyethylene was placed on top. The SMC was heated to a uniform temperature of 60°C. The resulting SMC was stiff, on cooling the polyethylene stripped cleanly off, and mouldings having low profile surfaces could be prepared directly from it without waiting for maturation to take place.

The aluminium hydroxy di-stearate was shown to be a suitable gelling agent for the above SMC process by mixing about 2 parts by weight of stearate in 12 parts by weight of styrene and heating the mixture with stirring. The mixture gelled on heating to 60°C.

I claim:

1. A process for the preparation of an unsaturated polyester resin based sheet moulding compound which comprises (i) impregnating a continuous web of fibrous reinforcement with a liquid unsaturated polyester resin system consisting essentially of an unsaturated polyester, a liquid copolymerisable monomer, a polymerisation initiator and a gelling agent for the copolymerisable monomer, said gelling agent being capable of forming stable gels of the copolymerisable monomer when heated to a temperature below the temperature at which cross-linking of the system occurs, (ii) subsequently heating the impregnated web to a temperature sufficient to cause the gelling agent to gel the copolymerisable monomer almost instantaneously and (iii) recovering from said heating a sheet moulding compound ready for use without further maturation.

2. A process as claimed in claim 1 wherein the amount of copolymerisable monomer is in the range 20 to 60% by weight based on the total weight of the unsaturated polyester resin and copolymerisable monomer.

3. A process as claimed in claim 1 wherein the gelling agent is an aluminium salt of octoic, lauric, oleic, palmitic or stearic acid.

4. A process as claimed in claim 1 wherein the aluminium salt molecule has one or two acid ions and the other ions are hydroxyl ions.

5. A process as claimed in claim 1 wherein the gelling agent is present in an amount of from 5.0 to 20.0% by weight, based on the weight of the copolymerisable monomer.

6. A process as claimed in claim 1 wherein the unsaturated polyester resin system constitutes from 25 to 35% by weight of the total weight of the sheet moulding compound.

7. A process as claimed in claim 1 wherein the sheet moulding compound contains from 20 to 35% by weight of glass fibre reinforcement.

8. A process as claimed in claim 7 wherein the glass fibre reinforcement is a chopped strand mat.

9. A process as claimed in claim 7 wherein the glass fibre reinforcement is loose chopped strands.

10. A process as claimed in claim 1 wherein the sheet moulding compound contains from 30 to 40% by weight of a mineral filler.

11. A process as claimed in claim 1 wherein the sheet moulding compound contains an agent to reduce mould shrinkage.

12. A process as claimed in claim 8 wherein a glass fibre mat is passed through the polyester resin system, interleaved between polyethylene films and passed through compression rollers.

13. A process as claimed in claim 9 wherein layers of polyester resin system are coated onto polyethylene films, glass fibres produced by chopping glass rovings are applied to at least one coated film, the two coated films are brought together to contact the two coatings and the resultant composite is passed through compression rollers.

14. A process as claimed in claim 7, wherein the glass fibre reinforcement is a continuous filament mat.

* * * * *